(12) United States Patent
Gao et al.

(10) Patent No.: US 9,302,126 B2
(45) Date of Patent: Apr. 5, 2016

(54) FIXATIVE POLYMER COMPATIBLE WITH HAIR STYLING COMPOSITION

(76) Inventors: Wei Gao, Fort Washington, PA (US); Linus Linder, Harleysville, PA (US); Miao Wang, Schwenksville, PA (US); Mark Westmeyer, Collegeville, PA (US); Fanwen Zeng, Belle Mead, NJ (US)

(*) Notice: Subject to any disclaimer, the term of this patent is extended or adjusted under 35 U.S.C. 154(b) by 123 days.

(21) Appl. No.: 13/183,822

(22) Filed: Jul. 15, 2011

(65) Prior Publication Data

US 2012/0027711 A1 Feb. 2, 2012

Related U.S. Application Data

(60) Provisional application No. 61/400,656, filed on Jul. 30, 2010.

(51) Int. Cl.
| | |
|---|---|
| *A61Q 5/06* | (2006.01) |
| *A61K 8/04* | (2006.01) |
| *A61K 8/81* | (2006.01) |
| *A61K 8/86* | (2006.01) |
| *C08F 220/10* | (2006.01) |

(52) U.S. Cl.
CPC . *A61Q 5/06* (2013.01); *A61K 8/046* (2013.01); *A61K 8/8152* (2013.01); *A61K 8/86* (2013.01); *A61Q 5/065* (2013.01); *C08F 220/10* (2013.01)

(58) Field of Classification Search
USPC .................................. 424/47, 70.1
See application file for complete search history.

(56) References Cited

U.S. PATENT DOCUMENTS

| 4,192,861 A | | 3/1980 | Micchelli et al. |
|---|---|---|---|
| 4,315,910 A | | 2/1982 | Nowak, Jr. et al. |
| 4,994,088 A | * | 2/1991 | Ando et al. ................ 8/426 |
| 5,290,548 A | * | 3/1994 | Goldberg et al. ......... 424/78.18 |
| 5,733,344 A | * | 3/1998 | Shiraishi et al. .................. 8/435 |
| 5,885,708 A | * | 3/1999 | Lu et al. ......................... 428/353 |
| 5,916,967 A | | 6/1999 | Jones et al. |
| 6,280,748 B1 | * | 8/2001 | Morita et al. ................ 424/401 |
| 6,794,475 B1 | * | 9/2004 | Bialke et al. .................. 526/320 |
| 6,802,993 B2 | * | 10/2004 | Momoda et al. .............. 252/586 |
| 2004/0033206 A1 | * | 2/2004 | Dubief et al. ............. 424/70.122 |
| 2004/0131566 A1 | * | 7/2004 | Hirata et al. .................. 424/70.1 |
| 2004/0225052 A1 | | 11/2004 | Bialke et al. |
| 2008/0314292 A1 | * | 12/2008 | Shimanaka .............. C09D 4/00 106/505 |

FOREIGN PATENT DOCUMENTS

| EP | 1504744 A1 | | 2/2005 | |
|---|---|---|---|---|
| GB | 2291893 A | | 2/1996 | |
| JP | H1-213221 | * | 8/1989 | ............... A61K 7/13 |
| JP | 8217513 A | | 8/1996 | |
| WO | 9535087 A1 | | 12/1995 | |

OTHER PUBLICATIONS

Notice of the Fourth Office Action for Chinese Patent Application No. 201110221873.1 dated Nov. 25, 2013.
European Search Report; European Application No. EP11174282; Dated Sep. 30, 2015; 3 pages.

* cited by examiner

*Primary Examiner* — Robert A Wax
*Assistant Examiner* — Amanda Heyes
(74) *Attorney, Agent, or Firm* — Edward L. Brant; Cantor Colburn LLP

(57) ABSTRACT

A polymer with good compatibility comprising one or more non-ionic water soluble monomers, such as poly(ethylene glycol)(meth)acrylate (PEGMA), is provided that is suitable for use in aerosol hair styling formulations which have improved clarity. There is also provided a hair styling composition comprising (a) one or more fully soluble polymer, and (b) a solvent mixture, and optional other ingredients.

18 Claims, No Drawings

FIXATIVE POLYMER COMPATIBLE WITH HAIR STYLING COMPOSITION

This application claims the benefit of priority under 35 U.S.C. §119(e) of U.S. Provisional Patent Application No. 61/400,656 filed on Jul. 30, 2010.

FIELD OF THE INVENTION

The present invention relates to fully soluble polymers, which include nonionic water-soluble monomers as polymerized units and which are useful as fixative resins in hair spray formulations, particularly in hair spray formulations having high VOC content.

BACKGROUND

Hair styling formulations are desired that provide both good hold (i.e., the ability to hold hair in place) and good shine (i.e., the ability to give hair a shiny appearance). Additionally, clarity (translucent appearance) of the hair styling formulation prior to application is aesthetically important to consumers.

Typically, hair styling formulations include one or more polymers which serve as the hair fixative. While there are many polymers that provide good hold in hair styling formulations, some of them negatively impact other properties such as shine or clarity.

Hair styling formulations also typically include an appropriate solvent. The class of volatile organic compounds (VOCs) which are liquid at 25° C. and one atmosphere pressure are generally useful as volatile organic solvents in hair spray formulations. Because hair styling formulations are sometimes sprayed, it is desirable that any polymers used in the formulation dissolve fully in the solvent. Further, for proper spraying, it is desirable that a solution of any polymers used in the composition should have viscosity that is not too high.

Where a hair styling formulation is to be applied in an aerosol spray, the solvent also includes one or more propellants, which may be volatile non-organic compounds or VOCs and are gaseous at 25° C. and one atmosphere pressure. For example, without limitation, it is known to use carbon dioxide, propane, isobutane, dimethyl ether and tetrafluoroethane, among other materials, as the aerosol propellant for such formulations.

It is also desirable that the hair styling formulation be stable (i.e., that none of the ingredients settles while the formulation is in storage). It is known that as the volatile organic compound (VOC) content of a formulation containing certain polymers increases, a haze appears, and increases, in the formulation, due to incompatibility of the polymer with solvents and propellants. This haze may negatively effect long term shelf life stability and also may be aesthetically unpleasing to consumers.

Thus, selecting the types and proportions of ingredients for hair styling formulations is very important and can be difficult. It is desired to provide polymers which have good hold characteristics, without negatively impacting the levels of shine and clarity in hair styling formulations.

One approach to improving the water compatibility of carboxylated vinyl polymeric hair spray resins in alcohol hydrocarbon propellant systems has been to neutralize at least a portion of the available carboxyl functionalities of the resins, as described in U.S. Pat. No. 4,192,861, using alkaline reagents.

U.S. Pat. No. 4,315,910 describes aerosol hair spray compositions used in aerosol metal containers that contain polymer, including, for example, styrene/maleic anhydride polymers, as well as carbon dioxide or hydrocarbon-alcohol propellants and 1-15% by weight water. It is asserted in U.S. Pat. No. 4,315,910 that addition of the water to this composition improved shelf stability and compatibility of the polymer in these compositions compared to anhydrous formulations using carbon dioxide or hydrocarbon-alcohol in aerosol metal containers.

It is also known to improve the clarity of non-aerosol, gel hair styling formulations containing silicone grafted co-polymers by neutralization with organic or inorganic neutralizer or mixtures thereof. GB 2291893A describes an aqueous/alcohol hair styling gel containing a silicone-containing polycarboxylic acid polymer and selected organic neutralizing agents that is claimed to have further improved clarity as well as non-sticky in-use feel and easy brush-out characteristics.

It has been discovered that some polymers, produced by emulsion polymerization and used in hair styling formulations, contain oligomer side products which increasingly precipitate and settle out of the formulation solution as the VOC content of the formulation increases. Thus, an object of the present invention was to identify and synthesize polymers having less oligomer side product or having oligomers which are more compatible with the VOCs used in hair styling formulations.

SUMMARY OF THE INVENTION

The present invention provides a polymer comprising, as polymerized units,
(i) 15% to 75% by weight, based on the weight of said polymer, of one or more monomers having a refractive index of 1.490 or higher;
(ii) 1% to 50% by weight, based on the weight of said polymer, of one or more non-ionic water soluble monomers having the formula:

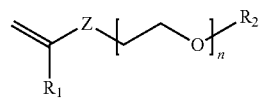

wherein $R_1$ is hydrogen or methyl;
Z is COO or CONH;
$R_2$ is hydrogen, a $C_1$-$C_{18}$ alkyl, phenyl, styrenol, or carboxylate;
and n is 1-50;
(iii) 1% to 30% by weight, based on the weight of said polymer, one or more acid-functional monomer; and
(iv) 5% to 69% by weight, based on the weight of said polymer, one or more additional monomer.

In one embodiment, the non-ionic water soluble monomer (ii) may be poly(ethylene glycol) (meth)acrylate and $R_1$ is hydrogen or methyl, Z is COO, and $R_2$ is hydrogen. In another embodiment, the non-ionic water soluble monomer (ii) is methyl poly(ethylene glycol) (meth)acrylate and $R_1$ is hydrogen or methyl, Z is COO, and $R_2$ is methyl. In still a further embodiment, the non-ionic water soluble monomer (ii) is alkyl poly(ethylene glycol) (meth)acrylate and $R_1$ is hydrogen or methyl, Z is COO, and $R_2$ is a $C_1$-$C_{18}$ alkyl.

The present invention also provide a hair styling composition which comprises (a) 1% to 10% by weight of one or more of the above-described fully soluble polymers, based on the total weight of said hair styling composition; and (b) 90% to 99% by weight a solvent mixture, based on the total weight of said hair styling composition. The solvent mixture comprises (i) 5% to 100% by weight volatile organic solvent, and (ii) 95% to 0% by weight water, based on the total weight of said solvent mixture. The solvent mixture may further comprise up to 75% by weight propellant, based on the total weight of the solvent mixture. In some embodiments, the propellant comprises dimethyl ether.

The present invention further provides a method for styling hair comprising the steps of placing said hair in a desired configuration and applying the hair styling composition described above to the hair.

In addition, the present invention provides a method for making a polymer comprising emulsion polymerization of one or more monomer mixture, wherein said monomer mixture comprises: (i) 15% to 75% by weight, based on the weight of said polymer, of one or more monomers having a refractive index of 1.490 or higher; (ii) 1% to 50% by weight, based on the weight of said polymer, of one or more non-ionic water soluble monomers having the formula:

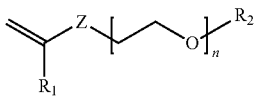

wherein $R_1$ is hydrogen or methyl;
Z is COO or CONH;
$R_2$ is hydrogen, a $C_1$-$C_{18}$ alkyl, phenyl, styrenol, or carboxylate; and n is 1-50;
(iii) 1% to 30% by weight, based on the weight of said polymer, one or more acid-functional monomer; and
(iv) 5% to 69% by weight, based on the weight of said polymer, one or more additional monomer,
wherein the emulsion polymerization is conducted partially or entirely in the presence of one or more nonionic surfactant and one or more chain transfer agent. In some embodiments, the chain transfer agent may comprise one or more alkyl mercaptan.

DETAILED DESCRIPTION

A "hair styling composition" as used herein is a composition that may be used on hair to hold the hair in a particular shape or configuration. Such compositions typically contain various polymeric resins, gums, and/or adhesive agents designed to impart desirable properties to the compositions and, ultimately, to hair upon which the compositions are applied. The polymers are used for a variety of purposes including, for example, one or more of hair holding, improving volume, improving appearance, and imparting desirable feel properties. Much of the ability of hair styling compositions to hold the hair in a particular shape results from one or more polymer used in the compositions. Hair styling compositions include, for example, hair sprays, styling gels, spray gels and mousses.

A "polymer," as used herein and as defined by F W Billmeyer, JR. in *Textbook of Polymer Science*, second edition, 1971, is a relatively large molecule made up of the reaction products of smaller chemical repeat units, which are referred to as "monomers," as defined in further detail below.

Polymer molecular weights can be measured by standard methods such as, for example, size exclusion chromatography (SEC, also called gel permeation chromatography, or GPC). Generally, polymers have weight-average molecular weight (Mw) of 1,000 Daltons or more. Some polymers are characterized by Mn, the number-average molecular weight.

As used herein "weight of polymer" means the dry weight of polymer. Molecules that can react with each other to form the repeat units of a polymer are known herein as "monomers." One example of a class of monomers that are useful in the present invention is, for example, ethylenically unsaturated monomers (i.e., monomers that have at least one carbon-carbon double bond). Typical ethylenically unsaturated monomers have molecular weight of less than 500. Among such monomers are, for example, vinyl monomers. Some suitable vinyl monomers include, for example, styrene, substituted styrenes, dienes, ethylene, ethylene derivatives, and mixtures thereof. Ethylene derivatives include, for example, unsubstituted or substituted versions of the following: vinyl acetate, acrylonitrile, (meth)acrylic acids, (meth)acrylates, (meth)acrylamides, vinyl chloride, halogenated alkenes, and mixtures thereof. As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof.

A polymer that is made by polymerizing a certain monomer, either alone or with other monomers, is said herein to include that monomer "as a polymerized unit."

As used herein, "normal boiling point" of a compound is the boiling point at one atmosphere pressure. As used herein, a "volatile" compound is a compound with normal boiling point of 250° C. or lower. As used herein, "INCI" is the International Nomenclature of Cosmetic Ingredients.

As used herein, an "organic" compound is any compound that contains one or more carbon atoms except for those carbon-containing compounds that are generally accepted to be inorganic compounds. Examples of carbon-containing compounds that are generally accepted to be inorganic compounds include, without limitation, the following: carbon oxides (such as, for example, carbon dioxide), carbon disulfide, metallic cyanides, metallic carbonyls, phosgene, carbonyl sulfide, metallic carbonates, and metallic bicarbonates.

It is useful to characterize hair styling compositions according to their VOC content. As used herein, the "VOC content" of a hair styling composition is the amount of all volatile organic compounds, expressed as a percentage by weight based on the total weight of the composition.

As used herein, "high-VOC" hair styling compositions are those in which the VOC content is between 55% and 99%, by weight, based on the total weight of the hair styling composition. For example, the VOC content of a high-VOC hair styling composition may be at least 75%, or even 90%. Independently, a high-VOC hair styling composition may have a VOC content of 90% or lower, or even 70% or lower.

As used herein, "low-VOC" hair styling compositions are those in which the VOC content is between 0% and 65%, by weight, based on the total weight of the hair styling composition. For example, the VOC content of a low-VOC hair styling composition may be between 35% and 65%; or even between 50% and 65%. Independently, a low-VOC hair styling composition may have a VOC content of 60% or lower.

The present invention provides a polymer for use in VOC-containing hair styling compositions having improved clarity and compatibility characteristics. More particularly, along with the typical monomers included in such polymers, i.e. those having a refractive index of 1.490 or higher, those which are acid-functional and others, the fully soluble polymer also comprises, as polymerized units, 1% to 50% by weight, based on the weight of the polymer, of one or more nonionic water soluble monomers having the formula:

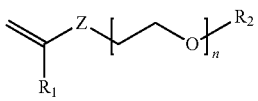

wherein $R_1$ is hydrogen or methyl; Z is COO or CONH; $R_2$ is hydrogen, a $C_1$-$C_{18}$ alkyl, phenyl, styrenol, or carboxylate; and n is 1-50. In some embodiments, n=12-26.

As used herein, "polymer with good compatibility" or "compatible polymer" means that the polymer meets the following criterion. A test solution including the polymer is made and tested for turbidity as described in the Examples section below. The composition of the test solution is comparable to the composition of a generic hair styling formulation including the polymer. Upon full neutralization, a polymer is considered herein to be compatible if it has turbidity of 120 Nephelometric Turbidity Units (NTU) or lower in a test solution with 12% or lower polymer solids (by weight based on the weight of the solution). If the polymer has turbidity of 10 NTU or lower, in a test solution with 12% polymer solids (by weight based on the weight of the solution), it is considered to have enhanced clarity. Thus, the "compatibility" of the polymer, as is meant herein, is determined based on the polymer's performance in a test solution. The test solution has a composition equivalent to a typical hair styling formulation and is analyzed and evaluated for stability, measured in NTUs, as described in detail hereinafter.

In some embodiments, the compatible polymer has "enhanced compatibility," which means herein that it has turbidity of 20 NTU or lower in a solution with 10% polymer solids (by weight based on the weight of the solution).

A polymer is considered herein to be compatible if and only if it meets the above criterion. It is contemplated that, in general, when a polymer that is fully compatible is observed in circumstances other than the turbidity test described below, it may be part of a system that is optically clear or may be part of a system that is turbid. For illustration, it is useful to consider an example polymer that was made by emulsion polymerization at pH of less than 6 and is observed in the form of the latex that was a produced by the emulsion polymerization; such an example polymer could be observed as having about 45% solids and having pH of less than 6. In some cases, such a latex could be turbid, and nevertheless, it is still possible that the polymer, when subjected to the turbidity test described below (which involves neutralization to higher pH and dilution with ethanol and water), could yield turbidity low enough that the polymer could qualify as "compatible" herein.

In some embodiments, polymer (a) is made by emulsion polymerization and exits in the form of a latex. In some of such embodiments, a portion of the complete latex is added to some appropriate solvent for the purpose, for example, of turbidity testing. In such cases, it is contemplated that latex that is added to the solvent will contain, in addition to the polymer itself, other compounds such as, for example surfactant or surfactants remaining in the latex from the emulsion polymerization process. When such a latex of polymer (a) of the present invention is tested, it will be shown to be fully soluble. That is, the test solution, which contains all of the compounds of the latex, will have sufficiently low turbidity.

It is contemplated that a latex of polymer (a) of the present invention can be fully compatible in the formulation even if one or more of the compounds present in the latex is not independently compatible with the formulation.

While the polymer with good compatibility of the present invention is hereinafter described in detail as a suitable component of hair styling compositions to be used as sprays, either aerosol or pump, it should be understood that the polymer having good compatibility of the present invention is also suitable for use in hair styling compositions which are to be used as gels, mousses, etc.

Hair spray compositions having high VOC content are particularly suitable for use as aerosol sprays. However, as mentioned hereinabove, high VOC-content hair styling compositions tend to suffer from diminished clarity, or haze, when components of the polymer fail to remain solubilized in the aqueous solvent mixture. Inclusion of one or more non-ionic water soluble monomers of the foregoing class increases the compatibility of the polymer and, therefore, improves clarity while still providing excellent hold properties.

The polymer with good compatibility of the present invention contains polymerized units of one or more monomer (known herein as "monomer (i)") that has refractive index of 1.490 or higher. Refractive index of a monomer can be measured, for example, by ASTM Standard D1218-02, at 25° C. In some embodiments, monomer (i) contains one or more monomer with refractive index of 1.500 or higher; or 1.530 or higher. In some embodiments, every monomer (i) is a monomer with refractive index of 1.530 or higher.

In some embodiments, monomer (i) contains one or more vinyl monomer. In some embodiments, monomer (i) contains one or more vinyl aromatic monomer. A vinyl aromatic monomer is a monomer that contains one or more carbon-carbon double bond and one or more aromatic ring. Suitable vinyl aromatic monomers include, for example, monomers with benzyl groups, monomers with phenyl groups, styrene, derivatives of styrene (such as, for example, alpha-methyl styrene), and mixtures thereof. In some embodiments, every monomer (i) is a vinyl aromatic monomer. In some embodiments, monomer (i) comprises one or more of styrene, alpha-methyl styrene, or a mixture thereof. In some embodiments, every monomer (i) is selected from styrene, alpha-methyl styrene, and mixtures thereof.

Mixtures of suitable monomers (i) are also suitable.

The amount of polymerized units of monomer (i) in the polymer with good compatibility of the present invention is 30% to 75% by weight, based on the weight of the polymer. In some embodiments, the amount of polymerized units of monomer (i) is 35% or more, or 39% or more, by weight, based on the total weight of the polymer. In some embodiments, the amount of polymerized units of monomer (i) is 65% or less, or 55% or less, by weight, based on the total weight of the polymer.

The polymer with good compatibility of the present invention additionally contains one or more polymerized unit of one or more nonionic water soluble monomers having the formula:

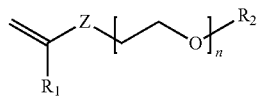

wherein $R_1$ is hydrogen or methyl; Z is COO or CONH; $R_2$ is hydrogen, a $C_1$-$C_{18}$ alkyl, phenyl, styrenol, or carboxylate; and n is 1-50. In some embodiments, n=12-26.

Suitable nonionic water-soluble monomers encompass, among others, acrylamide, $C_1$-$C_6$ N-alkylated or $C_1$-$C_3$ N,N- dialkylated acrylamides, polyethylene glycol acrylate, polyethylene glycol methacrylate, N-vinylacetamide, N-methyl-N-vinylacetamide, N-vinylformamide, N-methyl-N-vinylformamide, N-vinyl lactams hydroxyethyl acrylate, hydroxypropyl acrylate, hydroxyethyl methacrylate, hydroxypropyl methacrylate, and mixtures thereof.

Examples of commercially available nonionic water-soluble monomers suitable for inclusion in the compatible polymer of the present invention include, without limitation, the following:

Methoxy poly(ethylene glycol) monomethacrylates of Mws 300, 475, 1100, or 2100 or methoxy poly(ethylene glycol) monoacrylate having an Mw 426 from Aldrich Chemical Co. of Milwaukee, Wis., U.S.A.;

Visiomer® MPEG 750 MA, MPEG 1005 MA and MPEG 2005 from Evonik CYRO LLC of Osceola, Ark., U.S.A.;

SR 550, CD 551, CD 552 or CD 553 from Sartomer Chemicals of Exton, Pa., U.S.A.;

M-90G, M-230G, AM-90G (Methoxy poly(ethylene glycol 400) monoacrylate or AM-230G from Shin-Nakamura Chemicals of Wakayama, Japan;

Bisomer® PEM6 LD, PPM5 LI, MPEG350MA, MPEG550MA, S7W, S10W or S20W from Cognis Corporation of Cincinnati, Ohio;

Poly(ethylene glycol) monomethacrylates having Mw 200 or 400, Methoxy poly(ethylene glycol) monomethacrylate having Mw 200, 400 or 1000 and mono(succinimidyl succinate) ester of average molecular weight 1900 or 5000, from Polysciences, Inc. of Warrington, Pa., U.S.A.;

Poly(ethylene glycol) phenyl ether monoacrylates of Mw 236, 280 or 324, available from Aldrich Chemical Co.;

Methoxy poly(ethylene glycol 5000) 2-(vinylsulfonyl) ethyl ether from Fluka, a division of Sigma-Aldrich of Saint Louis, Mo., U.S.A.; and Ethoxy poly(ethylene glycol) monomethacrylate from Aldrich Chemical Co.

In some embodiments, the nonionic water-soluble monomer (ii) is selected from the group consisting of: a poly (ethylene glycol)(meth)acrylate (PEGMA), an alkyl-poly (ethylene glycol)(meth)acrylate, and mixtures thereof. In some embodiments, the nonionic water-soluble monomer (ii) is methoxy-poly(ethylene glycol) monomethacrylates.

Mixtures of suitable nonionic water-soluble monomers (ii) are also suitable.

The amount of polymerized units of the nonionic water-soluble monomer (ii) in the polymer is 1% to 50% by weight, based on the weight of the fully soluble polymer. In some embodiments, the amount of polymerized units of nonionic water-soluble monomer (ii) in the polymer is 2% or more, or 5% or more, or 10% or more, or 15% or more, or 20% or more, or 25% or more, or 30% or more, or 40% or more, by weight, based on the weight of the polymer.

The compatible polymer of the present invention further contains one or more polymerized unit of one or more monomer (herein called "monomer (iii)") having at least one acid-functional group. Suitable acid-functional groups include, for example, sulfonic acid groups and carboxylic acid groups. The acid-functional groups may be in neutral form or ionic form or a mixture thereof. Some suitable monomers (iii) include, for example, vinyl monomers with at least one acid-functional group. Independently, in some embodiments at least one monomer (iii) with a carboxylic acid group is used. In some embodiments, every monomer (iii) has a carboxylic acid group.

Suitable monomers (iii) having sulfonic acid group include, for example, 2-acrylamido-2-methylpropane sulfonic acid. Suitable monomers (iii) include, for example, acrylic acid, methacrylic acid, and mixtures thereof.

In some embodiments, monomer (iii) comprises at least one monomer that has exactly one acid-functional group.

In some embodiments, the compatible polymer of the present invention does not include any polymerized unit of maleic anhydride. In some embodiments, the compatible polymer of the present invention does not include any polymerized unit of any monomer with any anhydride group. In some embodiments, the compatible polymer of the present invention does not include any polymerized unit of any monomer with more than one carboxyl group. In some embodiments, the compatible polymer of the present invention does not include any polymerized unit of any monomer with more than one acid-functional group.

Mixtures of suitable monomers (iii) are also suitable.

The amount of polymerized units of monomer (iii) in the polymer is 1% to 30% by weight, based on the weight of the polymer. In some embodiments, the amount of polymerized units of monomer (iii) in the polymer is 2% or more; or 5% or more; or 10% or more; or 12% or more, or 14% or more, or 18% or more, or 20% or more, or 22% or more, by weight, based on the weight of the polymer.

In some embodiments, every monomer (i) that is present is a monomer that has no acid functional group. Independently, in some embodiments, every monomer (iii) that is present is a monomer that has index of refraction below 1.490. Also contemplated are embodiments in which every monomer (i) that is present is a monomer that has no acid functional group and in which every monomer (iii) that is present is a monomer that has index of refraction below 1.490.

Also contemplated are embodiments in which one or more monomer is used that has index of refraction of 1.490 or greater and also has at least one acid functional group. In such embodiments, it is contemplated to calculate the amount of polymerized units of monomers (i) and (iii) in the compatible polymer by finding the total weight of polymerized units of monomers that have index of refraction of 1.490 or greater or that have at least one acid functional group or that have both index of refraction of 1.490 and at least one functional group, counting each polymerized unit once. That total weight will be 31% to 95% by weight, based on the weight of the fully soluble polymer.

Among embodiments in which one or more monomer is used that has index of refraction of 1.490 or greater and also has at least one acid functional group, some suitable such monomers are, for example, styrenesulfonic acid and substituted styrene sulfonic acids.

The compatible polymer of the present invention additionally contains polymerized units of one or more additional monomer (known herein as "monomer (iv)"). Monomer suitable as monomer (iv) is monomer that is not any of monomers (i), (ii) or (iii). In some embodiments, monomer (iv) includes one or more vinyl monomer. In some embodiments, every monomer (iv) is a vinyl monomer.

Some suitable monomers (iv) include, for example, olefins, dienes, and (meth)acrylate monomers. As used herein, (meth) acrylate monomers include substituted and unsubstituted esters and amides of acrylic acid and methacrylic acid. Some suitable monomers (iv) include, for example, alkyl esters of (meth)acrylic acid, including, for example, those in which the alkyl group is linear, branched, cyclic, or a combination thereof, with 1 to 20 carbon atoms. In some embodiments, monomer (iv) includes one or more $C_1$-$C_{20}$ alkyl acrylate. In some embodiments, monomer (iv) includes one or more alkyl acrylate with 2 or more carbon atoms, or with 3 or more carbon atoms. Independently, in some embodiments, monomer (iv) includes one or more alkyl acrylate with 10 or fewer carbon atoms, or with 8 or fewer carbon atoms. In some embodiments in which one or more alkyl acrylate is used, the amount of polymerized units of alkyl acrylate monomer in the polymer is 5% or more, or 10% or more, by weight based on the weight of the polymer. Independently, in some embodiments in which one or more alkyl acrylate is used, the amount of polymerized units of alkyl acrylate monomer in the polymer is 50% or less, or 40% or less, by weight based on the weight of the polymer.

Independently, in some embodiments, monomer (iv) includes one or more $C_1$-$C_{20}$ alkyl methacrylate. In some embodiments, monomer (iv) includes one or more alkyl methacrylate with 6 or fewer carbon atoms, or with 3 or fewer carbon atoms, or with 2 or fewer carbon atoms. In some embodiments, monomer (iv) contains one or more alkyl acrylate and also contains one or more alkyl methacrylate. In some embodiments in which one or more alkyl methacrylate is used, the amount of polymerized units of alkyl methacrylate monomer in the polymer is 3% or more, or 6% or more, by weight based on the weight of the polymer. Independently, in some embodiments in which one or more alkyl methacrylate is used, the amount of polymerized units of alkyl methacrylate monomer in the polymer is 25% or less, or 12% or less, by weight based on the weight of the polymer.

Independently, some suitable monomers (iv) also include, for further example, substituted-alkyl esters of (meth)acrylic acid, which have the structure of alkyl esters of (meth)acrylic acid in which the ester group has one or more substituent group such as, for example, one or more hydroxyl group. Some suitable monomers (iv) include, for example, hydroxyalkyl esters of (meth)acrylic acid in which the alkyl group has 1 to 10 carbon atoms. In some embodiments, monomer (iv) contains one or more hydroxyalkyl ester of (meth)acrylic acid in which the alkyl group has 6 or fewer carbon atoms, or 4 or fewer carbon atoms. Some suitable hydroxyalkyl esters of (meth)acrylic acid include, for example, hydroxypropyl (meth)acrylate, hydroxyethyl (meth)acrylate, and mixtures thereof. In some embodiments in which one or more substituted-alkyl ester of (meth)acrylic acid is used, the amount of polymerized units of substituted-alkyl ester of (meth)acrylic acid in the polymer is 2% or more, or 5% or more, by weight based on the weight of the polymer. Independently, in some embodiments in which one or more substituted-alkyl ester of (meth)acrylic acid is used, the amount of polymerized units of substituted-alkyl ester of (meth)acrylic acid in the polymer is 40% or less, or 20% or less, by weight based on the weight of the polymer.

In some embodiments, monomer (iv) contains one or more alkyl acrylate, one or more alkyl methacrylate, and one or more substituted-alkyl (meth)acrylate.

In some embodiments, monomer (iv) does not contain any substituted-alkyl (meth)acrylate.

In some embodiments, the sum of the amount polymerized units of monomer (iii) plus the amount polymerized units of hydroxyalkyl esters of (meth)acrylic acid is, by weight based on the weight of the polymer, 10% or more, or 20% or more. Independently, in some embodiments, the sum of the amount of polymerized units of monomer (iii) plus the amount of polymerized units of hydroxyalkyl esters of (meth)acrylic acid is, by weight based on the weight of the polymer, 50% or less, or 40% or less.

In some embodiments, the amount of hydroxyalkyl esters of (meth)acrylic acid is 5% or less, or 0%, and the amount of monomer (iii) is 20% or more, by weight based on the weight of the polymer.

Independent of the composition of monomer (iv), the total amount in the compatible polymer of the present invention of polymerized units of all monomer or monomers (iv) is 30% to 89% by weight based on the weight of the fully soluble polymer. In some embodiments, the total amount of polymerized units of monomer (iv) is 75% or less, or 60% or less, by weight based on the weight of the fully soluble polymer.

Mixtures of suitable monomers (iv) are also suitable.

Independent of its composition, the compatible polymer has a Mw of between 25,000 and 300,000. For example, without limitation, in some embodiments, the compatible polymer of the present invention has a Mw of 25,000 or higher, or 50,000 or higher. Furthermore, in some embodiments, the compatible polymer independently has a Mw of 300,000 or lower, or 150,000 or lower.

The compatible polymer may be produced by emulsion polymerization. Emulsion polymerization is a well known process, described, for example, by M. S. El-Aasser in "Emulsion Polymerization" (Chapter 1 of *An Introduction to Polymer Colloids*, edited by F. Candau and R. H. Ottewill, Kluwer Academic Publishers, 1990).

One or more chain transfer agent may be used during polymerization to produce the fully soluble polymer. Chain transfer agents are compounds that are effective at promoting chain transfer process during free-radical polymerization. It is contemplated that chain transfer agents act to reduce the molecular weight of the polymer that is produced by the polymerization process. Some suitable chain transfer agents include, for example, mercaptans, sulfides, and halides. Some suitable halides, for example, include alkyl halides, such as, for example, halomethanes and halogenated esters (such as, for example, halogenated acetates). Suitable sulfides include, for example, dialkyl disulfides, diaryl disulfides, diaroyl disulfides, and xanthogens. Some suitable mercaptans include, for example, unsubstituted alkyl mercaptans and substituted alkyl mercaptans. Substituted alkyl mercaptans include, for example, compounds in which one or more hydroxyl group and/or one or more carboxyl group is attached to the alkyl portion of the molecule, in addition to the one or more thiol group. In some embodiments, one or more unsubstituted alkyl mercaptans may be used.

Where one or more chain transfer agents are used, the amount of chain transfer agent, in millimoles per 100 grams of total monomer, is between 0.5 and 20. For example, without limitation, 0.5 or more, or 1 or more, or even 2 or more, millimoles of chain transfer agent. Independently, the amount of chain transfer agent used, in millimoles per 100 grams of total monomer, is 20 or less; or 10 or less; or 5 or less.

Emulsion polymerization typically involves the use of one or more surfactant. Thus, in some embodiments, the emulsion process for producing the compatible polymer in accordance with the present invention may involve the use of one or more nonionic surfactant.

Suitable nonionic surfactants include, for example, polyoxyalkylene surfactants, polyalkylene glycol esters, polyoxyethylene derivatives of fatty acid esters of polyhydric alcohols, fatty acid esters of polyalkoxylated polyhydric alcohols, polyalkoxylated natural fats and oils, polyalkylene oxide block copolymers, and mixtures thereof. Among the suitable polyoxyalkylene surfactants, some suitable examples are polyoxyethylene surfactants, including, for example, alcohol alkoxylates, alkylphenol alkoxylates, and mixtures thereof. Suitable alcohol alkoxylates include, for example, alcohol ethoxylates and alcohol propoxylates. In some embodiments, one or more alcohol ethoxylate is used. In some embodiments, one or more secondary alcohol ethoxylate is used. In some embodiments, every nonionic surfactant used in the polymerization of the compatible polymer is a secondary alcohol ethoxylate.

In some embodiments, the amount of nonionic surfactant used in the emulsion polymerization is 0.5% to 12% by weight based on the total weight of monomers used in the polymerization. In some embodiments, the amount of nonionic surfactant, by weight based on the total weight of monomers used in the polymerization, is 1% or more; or 2% or more; or 5% or more. Independently, in some embodiments, the amount of nonionic surfactant, by weight based on the total weight of monomers used in the polymerization, is 10% or less; or 8% or less.

In some embodiments, no anionic surfactant is used in the emulsion polymerization process. In some embodiments, one or more anionic surfactant is used in the emulsion polymerization process in addition to the one or more nonionic surfactant. Suitable anionic surfactants include, for example, sulfosuccinates, sulfonates, sulfates, phosphonates and phosphates. Associated with each anionic surfactant is a cation; suitable cations include, for example, ammonium, cation of an alkali metal, and mixtures thereof.

Independently, in some embodiments, the emulsion polymerization process uses no cationic surfactant. Independently, in some embodiments, the emulsion polymerization process uses no anionic surfactant.

In some embodiments in which one or more anionic surfactant is used, one or more alkyl polyalkoxylate sulfate or phosphate surfactant is used. For example, alkyl polyalkoxylate sulfate has the structure

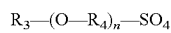

where $R_3$ and $R_4$ are alkyl groups and n is 1 to 1,000. In some embodiments, $R_3$ has 6 or more carbon atoms, or 8 or more carbon atoms. In some embodiments, $R_3$ is lauryl. In some embodiments, $R_4$ has 2 or 3 carbon atoms or a mixture thereof. In some embodiments, $—R_4—$ is $—CH_2CH_2—$. In some embodiments, n is 10 or higher, or 30 or higher, or 50 or higher. Independently, in some embodiments, n is 200 or lower, or 100 or lower, or 75 or lower. In some embodiments, every anionic surfactant that is used in the polymerization of polymer (a) (or polymer (AA)) is an alkyl polyalkoxylate sulfate surfactant.

In some embodiments in which one or more anionic surfactant is used, the amount of anionic surfactant is 0.02% to 1%, by weight based on the total weight of monomers used in the polymerization. Independently, in some embodiments in which one or more anionic surfactant is used, the amount of anionic surfactant is, by weight based on the total weight of monomers used in the polymerization, 0.01% or more; or 0.03% or more. Independently, in some embodiments in which one or more anionic surfactant is used, the amount of anionic surfactant is, by weight based on the total weight of monomers used in the polymerization, 0.8% or less; or 0.4% or less; or 0.2% or less.

In some embodiments, each surfactant is fully soluble. A surfactant is considered fully soluble herein if it passes the following test. The surfactant to be tested is added to 100% ethanol (200 proof, denatured) to form a test mixture. The amount of surfactant used in the test mixture is 0.50 g actives added to 20 g of ethanol. The solution is stirred for 5 minutes and tested for turbidity as described below. A soluble surfactant is taken to be one which has less than 100 NTU haze units by this test, and shows no visible precipitate after standing for 20 minutes.

In some embodiments, the compatible polymer of the present invention does not include any polymerized unit of any monomer that is a vinyl lactam. Independently, in some embodiments, the compatible polymer of the present invention does not include any polymerized unit of any monomer that is an amide of acrylic acid or an amide of methacrylic acid. Independently, in some embodiments, the compatible polymer of the present invention does not include any polymerized unit of any monomer that is an amide compound. Independently, in some embodiments, the compatible polymer of the present invention does not include any polymerized unit of vinyl acetate. Independently, in some embodiments, the compatible polymer of the present invention does not include any polymerized unit of any monomer that has molecular weight of 500 or greater.

In another aspect, the present invention also provides a hair styling composition which comprises 1% to 10%, by weight, based on the total weight of the composition, of the above-described compatible polymer having polymerized units of one or more nonionic fully-soluble monomers in accordance with the present invention. Furthermore, the hair styling composition of the present invention also comprises 90% to 99% by weight, based on the total weight of the composition, of a solvent mixture. In turn, the solvent mixture comprises: 5% to 100% by weight of a volatile organic solvent and 95% to 0% by weight water, based on the total weight of the solvent mixture.

Volatile organic solvents suitable for use in the hair styling composition of the present application are VOCs which are liquid at 25° C. and capable of dissolving the fully soluble polymer. In some embodiments, one or more volatile organic solvents are used that have a boiling point of 200° C. or lower, for example, 150° C. or lower, or even 100° C. or lower. Independently, in some embodiments, one or more volatile organic solvents are used that have a boiling point of 30° C. or higher, for example, 45° C. or higher, or even 60° C. or higher.

Some suitable volatile organic solvents include, for example, without limitation: hydrocarbons, which may be linear, cyclic, branched, or a combination thereof; ketones; ethers; furans; fully or partially halogenated hydrocarbons; alcohols; aromatic compounds; and mixtures thereof. In some embodiments, the volatile organic solvent contains one or more alcohol. Suitable alcohols include, for example, without limitation, $C_1$-$C_5$ hydrocarbons with a single hydroxy group. One suitable alcohol is ethyl alcohol.

Mixtures of suitable organic solvents are also suitable. In some embodiments, no volatile organic solvent other than one or more alcohols are included in the solvent mixture.

The volatile organic solvent is typically present in the solvent mixture in an amount of from 5% to 100%, by weight, based on the weight of the solvent mixture. For example, the solvent mixture may comprise between 5% and 90% of one or more suitable volatile organic solvents as described above.

In addition, the solvent mixture comprises between 95% and 0%, by weight of water, based on the weight of the solvent mixture. In some embodiments, for example, the amount of water present in the solvent mixture may be 10% to 50%, by weight, based on the weight of the solvent mixture.

In some embodiments, no propellant is used in component (b).

However, for embodiments in which the hair styling composition is intended to be used in an aerosol spray, an appropriate propellant is typically included in the solvent mixture. Propellants are gaseous at 25° C. and one atmosphere pressure. Some suitable propellants have normal boiling point of 24° C. or lower; or 0° C. or lower; or even –20° C. or lower. Independently, some suitable propellants have normal boiling point of –196° C. or higher; or –100° C. or higher; or even –50° C. or higher.

Some suitable propellants are, for example, alkanes having 4 or fewer carbon atoms, fluorinated hydrocarbons having 2 carbon atoms, dimethyl ether, and mixtures thereof. Some suitable propellants are, for example, n-butane, isobutane, propane, dimethyl ether (DME), 1,1-difluoroethane, tetrafluoroethane, and mixtures thereof. In some embodiments, the propellant contains one or more of DME, 1,1-difluoroethane, tetrafluoroethane, or any mixture thereof. In some embodiments, every propellant is selected from dimethyl ether, 1,1-difluoroethane, tetrafluoroethane, and mixtures thereof.

In some embodiments, one or more organic propellants are included in the solvent mixture. In some embodiments, every propellant that is used is organic.

Independent of the boiling point at one atmosphere pressure, some propellants, called "liquefied propellants," are liquid at 25° C. inside a pressurized aerosol can. Some of such liquefied propellants are, for example, halocarbons, hydrocarbons, or mixtures thereof. Some propellants, called "compressed gas propellants," remain gaseous at 25° C. inside a pressurized aerosol can.

In some embodiments, a water-soluble propellant is used (i.e., a propellant that is soluble in water at 25° C. at autogenous pressure). The autogenous pressure is the pressure inside a sealed aerosol can that arises from the volatility of the ingredients. One suitable water-soluble propellant is, for example, dimethyl ether (DME). In some embodiments, every propellant that is used is water-soluble. In some embodiments, the only propellant that is used is DME.

In embodiments which include one or more propellants, the total amount of propellant in the solvent mixture is typically 25% to 75%, by weight based on the weight of the solvent mixture. For example, the propellant may be present in an amount of 30% or more; or 45% or more; or even 50% or more, by weight, of the solvent mixture. Independently, the propellant may be present in an amount of 60% or less; or even 50% or less, by weight, based on the weight of the solvent mixture.

Overall, it is contemplated that, if two or more organic compounds that have normal boiling point of 250° C. or lower are used in the hair styling composition, they may or may not be mixed together prior to being added to the composition.

Independent of the degree of compatibility of the polymer, some embodiments of the hair spray composition are storage stable. That is, after storage in a closed container for 6 months, there is no visible precipitate and there is no change in the turbidity. In some embodiments, there is no visible precipitate and there is no change in the turbidity after storage for 18 months.

In some embodiments, there is a tendency for the hair styling composition to form foam. In some situations, such foam is undesirable. For example, the presence of air bubbles may reduce the shininess of treated hair. Among such embodiments, it is contemplated that a silicone defoamer may, optionally, be added to the hair styling composition. If a silicone defoamer is used, the weight ratio of silicone defoamer to polymer (a) may be, for example, from 0.01:1 to 0.5:1, or from 0.05:1 to 0.15:1.

For example, in one embodiment, the solvent mixture may comprise no propellant, 30% to 50% water, and 50% to 70% volatile organic solvent, by weight, based on the total weight of the solvent mixture. As another example, the solvent mixture may still comprise no propellant, but comprise 5 to 25% water and 75% to 90% volatile organic solvent, by weight. Still another embodiment may include 45% to 55% propellant, 30 to 45% water, and 0% to 25% volatile organic solvent, by weight, based on the total weight of the solvent mixture. In a further example, the solvent mixture may comprise, by weight, 40% to 60% propellant, 5% to 25% water, and 15% to 85% volatile organic solvent.

When the hair styling composition comprises a solvent mixture as described hereinabove, the amount of compatible polymer present in the hair styling composition of the present invention is 1% to 10%, by weight, based on the total weights of the composition. In some embodiments, for example, the amount of compatible polymer is 2% or more, or 3% or more, or 4% or more, by weight based on the sum of the total weight the composition. Independently, in some embodiments, the amount of compatible polymer used is 8% or less, or 6% or less, or 5% or less, by weight, based on the total weights the composition.

In addition to the foregoing components, the hair styling composition of the present invention may further comprise one or more neutralizing compounds. It is contemplated that compatible polymer is already soluble in the hair styling composition "as is." However, neutralization of some or all of the acid-functional groups contained in the compatible polymer increases compatibility and facilitates complete compatibility of the polymer in the composition. The acid-functional groups may be neutralized by conventional techniques with at least one neutralizing compound, which may aid in dissolving the compatible polymer in the hair styling composition. Neutralizing compound, when used, may be selected, for example, from one or more amines, alkali or alkaline earth metal hydroxides, ammonium hydroxide, and mixtures thereof. Suitable amine neutralizers include, for example, 2 amino-2-methyl-1,3-propanediol, 2-amino-2-methyl-1-propanol (AMP), N,N-dimethyl-2-amino-2-methyl-1-propanol, mono-isopropanolamine, triisopropanolamine, ethanolamine, triethanolamine, cyclohexylamine, morpholine, and mixtures thereof. Suitable alkali or alkaline earth metal hydroxides include, for example, sodium hydroxide and potassium hydroxide. In some embodiments, the neutralizer is selected from one or more of 2-amino-2 methyl-1,3-propanediol, 2 amino-2-methyl-1-propanol, N,N-dimethyl-2-amino-2-methyl-1-propanol, potassium hydroxide, triethanolamine, and triisopropanolamine. Mixtures of suitable neutralizing compounds are also suitable.

Among embodiments in which neutralizing compound is used, the molar equivalent ratio of neutralizing compound to acid-functional groups on polymer (a) is, for example, 0.05 or higher, or 0.1 or higher, or 0.5 or higher, or 0.75 or higher. Independently, among embodiments in which neutralizing compound is used, the molar equivalent ratio of neutralizing compound to acid-functional groups on polymer (a) is, for example, 1.2 or lower. As is well known and understood by persons of ordinary skill in the art, a suitable level of neutralizer is typically calculated based on the acid number of the fully soluble polymer, and it is recommended to neutralize 60-120% of the total acid groups in the polymer to achieve a clear and stable formulation with desirable performance characteristics. For example, the neutralizing compound may be provided in an amount which will accomplish neutralization of 80-100% of the acid groups of the fully soluble polymer.

One or more adjuvants may also be included in the hair styling composition of the present invention. For example, among embodiments in which one or more adjuvant is used, adjuvants may include, for example, one or more polymers other than the compatible polymer according to the present invention, one or more of preservatives (including, for example, one or more of organic acids, isothiazolones, iodopropynylbutyl carbamate, benzyl alcohol, imidazolidinylurea and alkyl parabens); thickeners; moisturizers (such as glycerine, hydrolyzed silk protein, and hydrolyzed wheat protein); conditioning agents such as panthenol; conditioning agents (U.S. Pat. No. 5,164,177 may be consulted for further general and specific details on suitable conditioning agents); emulsifiers; antistatic aids; extracts; proteins; vitamins; colorants; UV protectors; fragrances, and corrosion inhibitors. In some embodiments, no adjuvant is used.

In some embodiments in which one or more adjuvant is used, the ratio of the weight of the total amount of adjuvants to the weight of the compatible polymer is 0.01:1 or higher; or 0.05:1 or higher; or 0.1:1 or higher. Independently, in some embodiments in which one or more adjuvant is used, the ratio of the weight of the total amount of adjuvants to the weight of the compatible polymer is 1.4:1 or lower; or 1.2:1 or lower; or 1.1:1 or lower.

Among embodiments in which one or more polymers other than a compatible polymer in accordance with the present invention is used in the hair styling composition, the other polymer may be one or more hair fixative polymers such as, for example, without limitation, butyl acrylate/ethyl acrylate/methacrylic acid copolymers, poly(vinyl pyrrolidone)/vinyl acetate copolymers, octylacrylamide/acrylates/butylaminoethyl-methacrylate copolymers, vinylcaprolactam/vinyl-pyrrolidone/dimethylaminoethyl-methacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, and polyesters. Additional hair fixative polymers that may be useful for blending with the compatible polymer include, for example (by INCI name), PVP/VA copolymer, ethyl ester of PVM/MA copolymer, butyl ester of PVM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyester acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, PVP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, octylacrylamide/acrylates/butylaminoethyl methacrylate copolymer, vinyl caprolactam/VP/dimethylaminoethyl methacrylate copolymer, acrylates/t-butylacrylamide copolymer, acrylates/C1-2 succinates/hydroxyacrylates copolymer, acrylamide/sodium acryloyldimethyltaurate/acrylic acid polymer and mixtures thereof.

Among embodiments in which one or more polymer other than the compatible polymer is used in the hair styling composition of the present invention, the other polymer may be one or more rheology modifier polymers such as, for example, acrylates steareth-20 methacrylate copolymer, acrylates Beheneth-25 methacrylate copolymer, acrylates steareth-20 methacrylate crosspolymer, acrylates copolymer, acrylates/vinylneodecanoate crosspolymer, and mixtures thereof.

The water in the composition of the present invention may be introduced into the hair styling composition by any method. It is contemplated, for example, that water may be added directly to the hair styling composition. It is also contemplated, for example, that the compatible polymer may be made by emulsion polymerization to produce a polymer latex, and that latex, containing both the polymer and water, may be added to the hair styling composition. Also contemplated are embodiments in which some water is added to the hair styling composition both directly and as part of a polymer latex.

In some embodiments, the hair styling composition of the present invention is fully soluble. That is, when all ingredients except for propellant (if any is to be used) are mixed together, and the resulting solution is measured for turbidity as described in the Examples below, the turbidity result is 120 NTU or lower in a solution with 12% polymer solids or is 100 NTU or lower in a solution with 10% polymer solids.

It is to be understood that in the present specification and claims, all operations and measurements, unless stated otherwise in specific cases, are conducted at 25° C.

EXAMPLES

In the following examples, the following terms and test procedures are used:
BA=butyl acrylate
MMA=methyl methacrylate
HEMA=hydroxyethyl methacrylate
MAA=methacrylic acid
STY=styrene
BzA=benzyl acrylate
EHA=2-ethylhexyl acrylate
n-DDM=n-dodecyl mercaptan
t-DDM=t-dodecyl mercaptan
3-MBP=3-mercapto-butyl propionate
3-MPA=3-mercaptopropionic acid
15-S-40=Tergitol™ 15-S-40 secondary alcohol ethoxylate from Dow Chemical Co.
FES-61=Disponil™ FES-61 fatty alcohol polyglycol ether sulfate, sodium salt, from Cognis Co.
FES-77=Disponil™ FES-77 fatty alcohol ether sulfate, sodium salt, from Cognis Co.
AMP-95=Aminomethyl propanol, from Angus Chemical Co.
DS-4=sodium dodecylbenzensulfonate, Polystep™ A-16-22, from Stepan Co.
RS-610=Rhodafac™ RS-610-A-25, ammonium phosphate ester from Rhodia, Inc.
ALS=ammonium lauryl sulfate, Polystep™ B-7, from Stepan Co.

Molecular Weight

Samples were dissolved in tetrahydrofuran (THF)—2 mg solid polymer per ml of THF—shaken overnight, and filtered through a 0.45 micrometer polytetrafluoroethylene (PTFE) filter. Analysis was performed by size exclusion chromatography (SEC) using a liquid chromatograph including AGILENT™ Model 1100 isocratic pump, autosampler, degasser (all from Waldbronn, Co., Germany) and WATERS™ Model 2414 differential refractometer (Milford Co.), at 40° C. Column set contained three PLgel columns (5 micrometer, 300× 7.5 mm) connected in series, with respective pore sizes of 100, 1,000, and 10,000 Angstrom units. Injection volume was 100 microliter. Data acquisition and processing were performed using Cirrus™ Software, version 3.0, from Polymer Laboratories, UK. Molar mass data were determined via ten-point standard curve acquired from preparations of two commercially available, pre-weighed polystyrene reference mixes, using third order fitting. Reported quantities are Mw (weight-average molecular weight) and Mw/Mn (quotient obtained by dividing Mw by Mn, the number-average molecular weight). The designation "Mw (k)" means Mw divided by 1,000.

Preparation of Sample Solution at 12% Polymer Solids

Sample solution was prepared as follows. A sample of a latex or solution is neutralized with AMP-95, either by calculating the amount of AMP-95 to be equivalent to the acid groups on polymer (a) or by titrating to a pH value of 7.5. An amount of neutralized latex polymer is chosen to contain 6 grams of solid polymer. That chosen amount of neutralized latex polymer is mixed with 30.0 g ethanol and sufficient water to make the total weight of the solution 50.0 g.

Preparation of Sample Solution at 10% Polymer Solids

Same as the sample preparation at 12% (as described above) except that an amount of neutralized latex polymer is chosen to contain 5 grams of solid polymer.

Viscosity

The sample solutions were tested at 25° C. using Brookfield viscometer model DV-II+ at 12 rpm. The spindle was chosen to give a reading on the viscometer between 20 and 80 percent of full scale. Results are reported in milliPascal*seconds (mPa*s), which is equivalent to centipoise. Results are reported as V12 (viscosity in mPa*s of sample solution at 12% polymer solids) or V10 (viscosity in mPa*s of sample solution at 10% polymer solids).

A polymer is considered to have acceptable viscosity if V12 is 50 mPa*s or less or if V10 is 30 mPa*s or less.

Turbidity

A sample solution was placed in a vial of size 30 ml (1 ounce) and measured using HF Scientific Micro 100 Laboratory Turbidimeter, using specifications published by the United States Environmental Protection Agency as EPA method 180.1 (Nephelometric Method). Results are reported Nephelometric Turbidity Units (NTU)

Shine:

The tresses were evaluated in a shine box by six panelists. The shine results are a ranking of best (value of 1) to worst (value of 5). Results of the six panelists were averaged to give the rating.

Hold:

The "hold" property was evaluated by three different tests: Loop Deformation, Curl Retention, and High Humidity Curl Retention.

The Loop Deformation test measures the work to compress a curl of hair 25% of its initial diameter. Compression was repeated 5 times for each tress. Measurements were conducted at 21° C. (70° F.) and 46% humidity. A Dia-Stron MTT-175 (Dia-Stron Ltd) miniature tensile tester was used. Test conditions:

Compression=25%
Cycles=5
Rate=120 mm/min
Diameter=30 mm
Contact Force=5
Maximum Force=2000

Hair tresses were ER dark brown hair tresses; each tress was 2.0 g±0.1 g. The length of each uncurled hair tress was 200 mm Tresses were washed with clarifying shampoo and warm water and then air dried. Tresses were re-wet and curled onto a 65 mm×20 mm curler and held in place with a bobby pin. The curled tresses were air dried at 21° C. for 16 hours. Dry curled tresses were sprayed with an aerosol hairspray for 2 seconds on the front and back from a distance of 20.3 cm (8 inches). Curled, treated tresses were dried for a minimum of 2 h in a controlled environment at 25° C. (77° F.) and 44% humidity.

Aerosol sprays were formulated as follows (parts by weight): 50 parts dimethyl ether, 30 parts ethanol, 15 parts water, and 5 parts solid polymer and aminomethylpropanol. Just prior to testing, the curler was carefully removed from the tress without uncurling. The curled tress was placed in the miniature tensile tester and the work required for curl compression was measured. Work values are average of results for 3 tresses and are reported in units of gmf (i.e., gram force).

W1=work required for first compression
W5=work required for fifth compression
% SR=Stiffness Retention=100×W5/W1

The treated hair is considered to be acceptably stiff when the work required for compression is 200 gram force or higher. Stiffness Retention values of 90% or higher are acceptable.

High Humidity Curl Retention measures the ability of treated hair to hold its shape. Tresses (like those used in the Loop Deformation test) with initial uncurled length of 200 mm were washed with clarifying shampoo and warm water and then air dried. Tresses were re-wet and curled onto a 60 mm×20 mm curler and held in place with a bobby pin. The curled tresses were air dried at 21° C. for 16 h. Dry curled tresses were treated by spraying for 2 seconds on the front and back from a distance of 20.3 cm (8 inches). Curled, treated tresses were dried for a minimum of 1 h in a controlled environment at 25° C. (77° F.) and 44% humidity.

Curls were carefully removed from curler. Initial curl length was measured. Tresses were placed into a high humidity chamber (25° C., 88% humidity) and removed at intervals for measurement of tress length.

Aerosol sprays were formulated as in the Loop Deformation test. Each reported result is the average of three tresses. Reported quantities (in mm) are L0=initial curl length
L1=curl length after 1 hour
L4=curl length after 4 hours
L24=curl length after 24 hours Also reported is the percent curl retention at 24 hours ("% CR24"), which is calculated as follows:

$$\%CR24=100*(200-L24)/(200-L0)$$

Shampoo Removability

The hair tresses 20.32 cm (8 inch) long and 2.0±0.1 grams (European Brown Virgin Hair, obtained from International Hair Importers, New York) were stripped with alcohol, then washed with TRESemmé Deep Cleansing Shampoo. Hair tresses were treated with sprays, 2 seconds for both back and front of the hair swatches. Dried under room temperature, 50% Relative Humidity for 2 hr, then washed with TRESemme Deep Cleansing Shampoo. After drying overnight at 25° C., hair swatches were evaluated by panelist for feel and flaking vs. untreated hair. If the results showed no difference vs. untreated hair, it indicates excellent shampoo removability. If very minor flaking or coated feel is observed, it indicates good shampoo removability. For visible flaking and coated feel hair is considered poor to very poor shampoo removability.

Gloss

Gloss measurements were taken after the films were allowed to dry for 1 hours. The method for determining the gloss is described in "Annual Book of ASTM Standards," Section 15, Volume 15.04, Test Procedure ASTM D 1455 (2000). A Gardner Byk Micro-Tri-Gloss meter, catalog number 4520, was used to record 80°, 60° and 20° gloss.

Evaluation Experiment—Study Conducted to Identify Cause of Haze

The water soluble oligomers in serum phase of emulsion samples of polymers to be used as the polymer fixative in hair styling compositions were quantified by Gel Permeation Chromatography (GPC) analysis. The serum phase samples were prepared by centrifugation, the relative molecular weight and quantity of oligomer were determined by using poly(methyacrylate acid) narrow molecular weight standards. A WATERS HPLC system consists of 2690 separation model and 410 refractive index detector was used for GPC analysis. Aqueous buffer was used as eluent, and GPC columns for water soluble polymers were used for separation.

Higher level of oligomer was identified in the emulsion samples which were used in hair styling formulations that produced higher NTU readings.

TABLE 1

| Sample ID* | Formulation Clarity (NTU) | Oligomer level (mg/ml) | Oligomer Mw (k) |
|---|---|---|---|
| A | 9.8 | 2.4 | 4.3 |
| B | 7.8 | 2.5 | 2.7 |
| C | 7.7 | 2.2 | 5.0 |
| D | 6.3 | 1.9 | 3.2 |
| E | 5.6 | 1.5 | 2.3 |
| F | 5.3 | 1.4 | 2.8 |
| G | 4.5 | 1.2 | 2.6 |
| H | 4.4 | 1.0 | 2.4 |
| I | 3.6 | 0.97 | 2.4 |
| J | 3.5 | 0.87 | 2.3 |
| K | 3.4 | 0.345 | 1.6 |

*These formulation samples were prepared using the procedure outlined in Example 5 below.

Example 1

PEGMA-containing Polymer Used in Hair Styling Formulations Sample Showed Positive Impact on Clarity Properties Formulation clarity was measured based on formulation that contains:

| | |
|---|---|
| Ethanol | q.s. to 100% w/w |
| Polymer | 12.5% w/w as is |
| AMP* | 1.33% w/w |
| Diethyl Ether | 50% w/w |

The clarity of the above formulation, using polymers prepared according to the following Example 5, 6 and 7, was measured by Turbidimeter Micro 100 Serial No. 202230 by Scientific, Inc. (Fort Myers, Fla.). An NTU reading of less than 6.0 is desired and considered to be a "clear" formulation. The higher the NTU reading, the hazier the appearance of the hair styling formulation. The results are presented in Tables 2 and 3 below.

TABLE 2

| Formulation Sample ID (containing NO PEGMA) | Polymer Preparation Method | Formulation clarity (NTU) |
|---|---|---|
| FS1 | Example 5 | 11.2 |
| FS2 | Example 5 | 9.7 |
| FS3 | Example 5 | 9.2 |
| FS4 | Example 5 | 8.3 |

TABLE 3

| Formulation Sample ID (containing PEGMA) | Polymer Preparation Method | Formulation clarity (NTU) |
|---|---|---|
| FS5 | Example 6 | 4.5 |
| FS6 | Example 6 | 4.6 |
| FS7 | Example 6 | 4.3 |

TABLE 3-continued

| Formulation Sample ID (containing PEGMA) | Polymer Preparation Method | Formulation clarity (NTU) |
|---|---|---|
| FS8 | Example 6 | 4.9 |
| FS9 | Example 7 | 3.5 |
| FS10 | Example 7 | 2.8 |
| FS11 | Example 7 | 3.5 |

Example 2

Use of PEGMA-containing Polymer in Hair Styling Formulation has No Negative Impact on Hold Performance Hair stiffness evaluation by Dia-stron curl compression test.

The hair tresses (European Brown Virgin Hair, obtained from International Hair Importers, New York) prior to curling were on the average 8 inches long and weighed 2.0±0.1 grams. They were washed using Tressemme Deep Cleansing Shampoo, then curled wet onto a 22 millimeter (mm)×70 mm curler and held in place with a bobby pin. The curled tresses were allowed to dry on the lab bench overnight, or in 45° C. oven for 1 hr.

Spray the curled tresses with test formulations from a distance of 30 cm in the hood, 1 seconds for both front and back of the curls. The curled, treated tresses were dried in 45° C. oven for 1 hour. Before the curl compression testing, the curler was removed carefully without disturbing the tress. The curled tress was placed on the miniature tensile tester, model MTT160 instrument (Dia-Stron Limited, UK). The curl was compressed to 25% of its initial diameter, the force-displacement curve was recorded. Peak force F(mgf) is reported to characterize curl stiffness.

TABLE 4

| Sample ID | Peak Stiffness (gmf) |
|---|---|
| FS11 (contains PEGMA) | 117.7 |
| FS4 (no PEGMA) | 91.6 |

Example 3

Use of PEGMA-containing Polymer in Hair Styling Formulation has No Negative Impact on Humidity Resistance Performance Curled tresses were prepared and treated as in the Diastron curl compression test above. After drying, the curlers were gently removed from tress and curls were suspended by clips in a humidity chamber at 90% RH, 25° C. Initial curl length was recorded. The length of the curled tresses was recorded at intervals over 4 h. Curl retention is determined as [(L(0)−L(t))/L(0)−L(i))×100] where L(0) is fully extended curl length, L(i) is initial curl length and L(t) is curl length at a specific time.

TABLE 5

| Sample ID | Curl retention (%) |
|---|---|
| FS11 (contains PEGMA) | 36 |
| FS4 (no PEGMA) | 32 |
| FS10 (contains PEGMA) | 48 |
| FS2 (no PEGMA) | 40 |

Example 4

Use of PEGMA-containing Polymer in Hair Styling Formulation has Positive Impact on Shine Performance Shine Measurement by Bossa Nova SAMBA 2.1

Untreated hair swatches 8 inches long, weigh 2 g (European Dark Brown Hair, International Hair Importer, NYC, NY) were first positioned and mounted on cylinder for initial baseline measurement. Hair swatches were then sprayed at 30 cm distance for 1 second, and air dried for 30 minutes before measurement. Each sample was repeated on 5 hair swatches.

The data collected was then computed by different equations and theories that consider various band geometery of the specular and diffused profile. We based our calculation on Reich-Robbins equation: $100*S(\text{specular})/D(\text{diffused})*\theta_0$ (reflection angle). Percentage of shine before and after treatment was calculated as a measure of shine improvement.

TABLE 6

| Sample ID | Shine Improvement (%) |
| --- | --- |
| FS11 (contains PEGMA) | 30 |
| FS4 (no PEGMA) | 23 |
| FS10 (contains PEGMA) | 35 |
| FS2 (no PEGMA) | 30 |

Example 5

Preparation of Polymer Having Good Compatibility

To a 5-liter, 4-necked round bottom flask equipped with a mechanical stirrer, thermocouple, condenser and nitrogen sparge was added 630 gms of deionized water. The reactor was purged with nitrogen and warmed to 90° C. A monomer pre-emulsion was prepared from 1077 gm of deionized water, 34.7 gm of Rhodafac RS610A25, 33.5 gm of benzoic acid powder, 14.5 gm of Disponil FES-993, 6.9 gm of n-dodecyl mercaptan (nDDM), 602.1 gm of styrene (STY), 550.5 gm of butyl acrylate (BA), 86.0 gm of 2-ethylhexyl acrylate (2-EHA), 86.0 gm of methyl methacrylate (MMA) and 387.0 gm of glacial methacrylic acid (MAA). At ~90° C. reactor temperature, the reactor was charged with a solution composed of 13.9 gm of Rhodafac RS610A25, 15 gm of deionized water, 115.5 gm of the monomer emulsion, 8.7 gm of glacial MAA and a solution composed of 1.7 gm of ammonium persulfate and 30 gm of deionized water. The reactor was held at ~88° C. for ~10 minutes. After this time, the monomer emulsion and initiator solution composed of 1.7 gm of ammonium persulfate and 226 gm of deionized water were fed over 3 hours at 15.4 and 1.3 gm/min, respectively. The reactor temperature was maintained between 87-89° C. After these additions were completed, the monomer emulsion and initiator feed lines were rinsed with 66 gm and 20 gm of deionized water, respectively. The reactor was then maintained at 88° C. for 30 minutes. After this hold had been completed, the latex was treated with the following solutions comprised of 0.023 gm of ferrous sulfate heptahydrate and 10 gm of water, 5.4 gm of t-butyl hydroperoxide and 147 gm of deionized water and 3.4 gm of Bruggolite FF-6 and 147 gm of deionized water. The reactor was cooled to 50° C. during these additions. The resulting latex was isolated and analyzed for % solids, pH, residual monomer, particle size, gel content and viscosity. Additional testing was conducted by formulating this latex to determine its formulation viscosity and clarity.

Example 6

Preparation of Polymer Having Good Compatibility

To a 5-liter, 4-necked round bottom flask equipped with a mechanical stirrer, thermocouple, condenser and nitrogen sparge was added 645 gms of deionized water. The reactor was purged with nitrogen and warmed to 90° C. A monomer pre-emulsion was prepared from 1038 gm of deionized water, 34.6 gm of Rhodafac RS610A25, 33.4 gm of benzoic acid powder, 14.4 gm of Disponil FES-993, 3.5 gm of n-dodecyl mercaptan (nDDM), 3.5 gm of 3-MPA, 605.4 gm of STY, 588.1 gm of BA, 86.5 gm of 2-EHA, 86.5 gm of methoxy poly (ethyl glycol, Mw-350) monomethacrylate and 388.2 gm of glacial MAA. At ~90° C. reactor temperature, the reactor was charged with a solution composed of 13.8 gm of Rhodafac RS610A25, 10 gm of deionized water, 115.2 gm of the monomer emulsion, 8.7 gm of glacial MAA and a solution composed of 1.7 gm of ammonium persulfate and 25 gm of deionized water. The reactor was held at ~88° C. for ~10 minutes. After this time, the monomer emulsion and initiator solution composed of 1.7 gm of ammonium persulfate and 225 gm of deionized water were fed over 3 hours at 15.3 and 1.2 gm/min, respectively. The reactor temperature was maintained between 87-89° C. After these additions were completed, the monomer emulsion and initiator feed lines were rinsed with 100 gm and 60 gm of deionized water, respectively. The reactor was then maintained at 88° C. for 30 minutes. After this hold had been completed, the latex was treated with the following solutions comprised of 0.022 gm of ferrous sulfate heptahydrate and 10 gm of water, 5.4 gm of t-butyl hydroperoxide and 146 gm of deionized water and 3.4 gm of Bruggolite FF-6 and 146 gm of deionized water. The reactor was cooled to 50° C. during these additions. The resulting latex was isolated and analyzed for % solids, pH, residual monomer, particle size, gel content and viscosity. Additional testing was conducted by formulation this latex to determine its formulation viscosity and clarity.

Example 7

Preparation of Polymer Having Good Compatibility

To a 5-liter, 4-necked round bottom flask equipped with a mechanical stirrer, thermocouple, condenser and nitrogen sparge was added 641 gms of deionized water. The reactor was purged with nitrogen and warmed to 90° C. A monomer pre-emulsion was prepared from 923 gm of deionized water, 34.1 gm of Rhodafac RS610A25, 32.9 gm of benzoic acid powder, 14.2 gm of Disponil FES-993, 1.8 gm of nDDM, 4.4 gm of 3-MPA, 605.4 gm of styrene, 553.5 gm of BA, 86.5 gm of 2-EHA, 155.7 gm of a Visiomer® MPEG 750 MA and 397.8 gm of glacial MAA. At ~90° C. reactor temperature, the reactor was charged with a solution composed of 13.6 gm of Rhodafac RS610A25, 10 gm of deionized water, 112.3 gm of the monomer emulsion, 17.3 gm of Visiomer® MPEG 750 MA and a solution composed of 2.6 gm of ammonium persulfate and 25 gm of deionized water. An exothermic reaction was observed within ~2 minutes and reached peak temperature within 20 minutes. Peak rate of change for the temperature during the seed initiation was 0.5° C. After the seed initiation reached peak temperature, the monomer emulsion and initiator solution composed of 1.7 gm of ammonium persulfate and 222 gm of deionized water were fed over 3 hours at 15.0 and 1.2 gm/min, respectively. The reactor temperature was maintained between 84-86° C. After these additions were completed, the monomer emulsion and initiator feed lines were rinsed with 99 gm and 49 gm of deionized water, respectively. The reactor was then maintained at 88° C. for 30 minutes. After this hold had been completed, the latex was treated with the following solutions comprised of 0.022 gm of ferrous sulfate heptahydrate and 10 gm of water was added to the reactor, 5.4 gm of t-butyl hydroperoxide and 158 gm of deionized water and 3.3 gm of Bruggolite FF-6 and 158 gm of deionized water. The reactor was cooled to 50° C. during these additions. The resulting latex was isolated and analyzed for % solids, pH, residual monomer, particle size, gel content and viscosity. Additional testing was conducted by formulation this latex to determine its formulation viscosity and clarity.

We claim:

1. A fixative polymer for a hair styling composition, the polymer in the form of a latex made by emulsion polymerization, having a weight-average molecular weight of 50,000 to 300,000, and comprising, as polymerized units,
    (i) 15% to 75% by weight, based on the weight of said polymer, of one or more monomers having a refractive index of 1.490 or higher;
    (ii) 2% to 15% by weight, based on the weight of said polymer, of one or more non-ionic water soluble monomers having the formula:

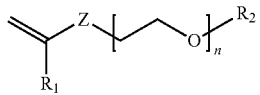

wherein $R_1$ is hydrogen or methyl;
Z is —(C=O)O— or —(C=O)NH—;
$R_2$ is hydrogen, a $C_1$-$C_{18}$ alkyl, phenyl, styrenol, or carboxyl;
and n is 1-50;
    (iii) 12% to 30% by weight, based on the weight of said polymer, of one or more acid-functional monomer; and
    (iv) 5% to 69% by weight, based on the weight of said polymer, of one or more additional monomer, with the proviso that said one or more additional monomer is different from monomers (i), (ii) and (iii), and is selected from the group consisting of olefins, dienes, $C_{1-20}$ alkyl (meth)acrylate monomers, $C_{1-10}$ hydroxyalkyl (meth)acrylate monomers, and a combination thereof.

2. The polymer according to claim 1, wherein said non-ionic water soluble monomer (ii) is poly(ethylene glycol) (meth)acrylate and $R_1$ is hydrogen or methyl, Z is COO, and $R_2$ is hydrogen.

3. The polymer according to claim 1, wherein said non-ionic water soluble monomer (ii) is methyl poly(ethylene glycol) (meth)acrylate and $R_1$ is hydrogen or methyl, Z is COO, and $R_2$ is methyl.

4. The polymer according to claim 1, wherein said non-ionic water soluble monomer (ii) is alkyl poly(ethylene glycol) (meth)acrylate and $R_1$ is hydrogen or methyl, Z is COO, and $R_2$ is a $C_1$-$C_{18}$ alkyl.

5. The polymer according to claim 1, wherein said monomer (i) comprises one or more vinyl aromatic monomer.

6. A hair styling composition comprising:
    (a) 1% to 10% by weight of one or more fully soluble polymers according to claim 1, based on the total weight of said hair styling composition; and
    (b) 90% to 99% by weight a solvent mixture, based on the total weight of said hair styling composition,
    said solvent mixture comprising:
        (i) 5% to 100% by weight volatile organic solvent, and
        (ii) 95% to 0% by weight water,
        based on the total weight of said solvent mixture.

7. The hair styling composition according to claim 6, wherein said solvent mixture further comprises:
    (iii) up to 75% by weight propellant, based on the total weight of the solvent mixture.

8. The hair styling composition according to claim 7, wherein said propellant comprises dimethyl ether.

9. The hair styling composition according to claim 6, further comprising:
    (d) a neutralizer, wherein the mole ratio of said neutralizer to the acid-functional groups on said polymer (a) is from 0:1 to 1.2:1, and
    (e) optionally, one or more adjuvants, wherein the ratio of the total weight of all adjuvants to the weight of said polymer (a) is from 0 to 1.4:1.

10. A method for styling hair comprising the steps of placing said hair in a desired configuration and applying the composition of claim 6 to said hair.

11. A method for making a polymer in the form of a latex having a weight-average molecular weight of 50,000 to 300,000 comprising emulsion polymerization of one or more monomer mixture, wherein said monomer mixture comprises
    (i) 15% to 75% by weight, based on the weight of said polymer, of one or more monomers having a refractive index of 1.490 or higher;
    (ii) 2% to 15% by weight, based on the weight of said polymer, of one or more non-ionic water soluble monomers having the formula:

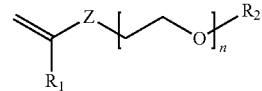

wherein $R_1$ is hydrogen or methyl;
Z is —(C=O)O— or —(C=O)NH—;
$R_2$ is hydrogen, a $C_1$-$C_{18}$ alkyl, phenyl, styrenol, or carboxyl;
and n is 1-50;
    (iii) 12% to 30% by weight, based on the weight of said polymer, of one or more acid-functional monomer; and
    (iv) 5% to 69% by weight, based on the weight of said polymer, of one or more additional monomer, with the proviso that said one or more additional monomer is different from monomers (i), (ii) and (iii), and is selected from the group consisting of olefins, dienes, $C_{1-20}$ alkyl (meth)acrylate monomers, $C_{1-10}$ hydroxyalkyl (meth)acrylate monomers, and a combination thereof, and
    wherein said emulsion polymerization is conducted partially or entirely in the presence of one or more nonionic surfactant and one or more chain transfer agent.

12. The method of claim 11, wherein said chain transfer agent comprises one or more alkyl mercaptan.

13. The method of claim 11, wherein the amount of said chain transfer agent is 0.5 to 20 millimoles per 100 grams of said monomer mixture.

14. The polymer of claim 1, wherein the amount of said monomer (iii) is 14% to 30% by weight, based on the weight of said polymer.

15. The polymer of claim 1, wherein the amount of said monomer (iii) is 20% to 30% by weight, based on the weight of said polymer.

16. The polymer of claim 1, wherein monomer (iii) is an acid-functional monomer comprising a sulfonic acid group, a carboxylic acid group, or a combination thereof.

17. The polymer of claim 16, wherein monomer (iv) is a $C_{1-20}$ alkyl (meth)acrylate, a $C_{1-10}$ hydroxyalkyl (meth)acrylate), or a combination thereof.

18. The polymer of claim 1, wherein monomer (iv) is a $C_{1-20}$ alkyl (meth)acrylate, a $C_{1-10}$ hydroxyalkyl (meth)acrylate), or a combination thereof.

* * * * *